(12) United States Patent
Barsky et al.

(10) Patent No.: US 8,328,858 B2
(45) Date of Patent: Dec. 11, 2012

(54) INFRARED WOUND HEALING UNIT

(75) Inventors: Barry E. Barsky, Havertown, PA (US);
Jay M. Silverman, Huntingdon Valley, PA (US)

(73) Assignee: Solar Light Company, Inc., Glenside, PA (US)

( * ) Notice: Subject to any disclaimer, the term of this patent is extended or adjusted under 35 U.S.C. 154(b) by 382 days.

(21) Appl. No.: 12/767,206

(22) Filed: Apr. 26, 2010

(65) Prior Publication Data
US 2011/0264175 A1 Oct. 27, 2011

(51) Int. Cl.
*A61N 5/06* (2006.01)
(52) U.S. Cl. ............... 607/90; 607/88; 606/9; 606/2
(58) Field of Classification Search ............ 607/90, 607/88; 606/2, 9
See application file for complete search history.

(56) References Cited

U.S. PATENT DOCUMENTS

| | | | |
|---|---|---|---|
| 5,086,763 A | 2/1992 | Hathman | |
| 5,119,467 A | 6/1992 | Barsky et al. | |
| 5,285,054 A | 2/1994 | Barsky | |
| 5,285,519 A | 2/1994 | Barsky et al. | |
| 5,352,869 A | 10/1994 | Barsky | |
| 5,498,229 A | 3/1996 | Barsky et al. | |
| 5,649,896 A | 7/1997 | Barsky | |
| 5,986,163 A * | 11/1999 | Augustine | 602/42 |
| 6,093,160 A * | 7/2000 | Augustine et al. | 602/2 |
| 6,213,965 B1 | 4/2001 | Augustine et al. | |
| 6,679,830 B2 | 1/2004 | Kolarovic et al. | |
| 2002/0165472 A1 | 11/2002 | Augustine et al. | |
| 2004/0138602 A1 * | 7/2004 | Rossen | 602/41 |
| 2006/0253089 A1 * | 11/2006 | Lin | 604/301 |
| 2007/0104664 A1 | 5/2007 | Maltezos et al. | |
| 2007/0233208 A1 * | 10/2007 | Kurtz et al. | 607/88 |

FOREIGN PATENT DOCUMENTS

| | | | |
|---|---|---|---|
| WO | 9831310 A1 | 7/1998 | |
| WO | 9846179 A1 | 10/1998 | |
| WO | 2004041064 A2 | 5/2004 | |
| WO | 2004041064 A3 | 5/2004 | |
| WO | 2006119473 A2 | 11/2006 | |

OTHER PUBLICATIONS

Harry T. Whelan, et al. "Effect of NASA Light-Emitting Diode Irradiation on Wound Healing" Journal of Clinical Laser Medicine & Surgery, vol. 19, No. 6, 2001, Mary Ann Liebert, Inc. pp. 305-314.

(Continued)

*Primary Examiner* — Kinam Park
(74) *Attorney, Agent, or Firm* — Barley Snyder (57) ABSTRACT

An infrared wound healing unit having a layer of an optically and radiographically transparent flexible heating element which, when powered, emits heat that serves to heal a wound according to monochromatic infrared energy (MIRE) treatment of the wound. This infrared wound healing unit is arranged so that:
(a) heat emitted from the layer of an optically and radiographically transparent flexible heating element passes to a wound of a patient to treat the wound,
(b) the wound of the patient that is being treated can be viewed while heat is emitted from the layer of an optically and radiographically transparent flexible heating element to treat the wound,
(c) the wound is accessible for other forms of treatment, and
(d) the infrared wound healing unit remains secured to the patient while the wound is being viewed or treated.

21 Claims, 4 Drawing Sheets

OTHER PUBLICATIONS

Rachel Lubart, et al. "A New Light Device for Wound Healing", Recent Patents on Biomedical Engineering 2008, vol. 1, No. 1, pp. 13-17.

Justin F. Schneiderman, "Electromagnetic Radiation Therapy in the Infrared Range", http://www-scf.usc.edu/~justinsc/Field_Therapy/info.html, Oct. 19, 2000.

Huseyin Demir, et al. "A Comparative Study of the Effects of Electrical Stimulation and Laser Treatment on Experimental Wound Healing in Rats", Journal of Rehabilitation Research & Development, vol. 41, No. 2, pp. 147-154, Mar./Apr. 2004.

Susan Mendez-Eastman, RN: "New Advances in Wound Therapy", http://www.wounds1.com/hero/hero_pf.cfm?ArticleID=8, Apr. 15, 2005.

Aaron M Flickstein, "Infrared Thermal System", http://lifestylelaboratory.com/articles/flickstein.html, 1994.

Mimi Leong, "Poststimulation Using Low Energy Lasers and Light Emitting Diode Therapy to Modulate Wound Healing" Wound Healing Society, (two pages), publication and publication date not known.

Exchanges between various individuals on "The LED light that heals" (5 pages), publication and publication date not known.

PCT Written Opinion of the International Searching Authority for International Application No. PCT/US20111/033739, Applicant, Solar Light Company, Inc., 7 pages.

PCT Notification of Transmittal of the International Search Report and the Written Opinion of the International Searching Authority, or the Declaration, International Application No. PCT/US2011/033739.

* cited by examiner

INFRARED WOUND HEALING UNIT

FIELD OF THE INVENTION

The present invention relates, in general, to the treatment and healing process of wounds and, in particular, to a wound healing unit that applies monochromal infrared energy to a wound to treat the wound and accelerate the healing process of the wound.

BACKGROUND

Skin contact monochromatic infrared energy (MIRE) therapy, also known as near-infrared energy therapy, involves delivering monochromatic infrared energy to a wound, whereby significant levels of heat are applied to the wound to accelerate the healing of the wound. MIRE therapy triggers the release of nitric oxide from the hemoglobin in the blood and proteins in the tissue being treated. Nitric oxide is a molecule produced by the body that is known to dilate arteries, veins, and lymphatic vessels, thereby improving circulation, decreasing swelling, and alleviating pain. In addition, the release of nitric oxide is believed to stimulate angiogenesis, or the process by which new blood vessels are created during healing and growth. Based on these properties, MIRE therapy has been proposed for the treatment of a wide variety of conditions, including muscle soreness, diabetic neuropathy, tendonitis, lymphedema, myofascial pain, temporomandibular disorders, and chronic skin ulcers.

MIRE therapy is conducted using equipment that transmits infrared energy to the site of the wound. A patient is treated and, after treatment, leaves the area where the equipment is located. The healing process is monitored and, if additional MIRE treatment is required, the patient returns for more treatment. Oftentimes, patients receive multiple MIRE therapy treatments that are spread over extended periods of time.

Multiple MIRE treatments require multiple trips to and from the location of the MIRE therapy equipment. Such trips might be as short as moving the patient from the patient's hospital room to the hospital MIRE therapy facility where the MIRE therapy equipment is located. In addition, the scheduling of MIRE therapy treatment can become a problem when the demand for access to the therapy equipment is high. Oftentimes, the nature of the wound is such that it is not necessary that treatment of the wound requires the services of a professional who is trained and experienced in MIRE therapy and the operation of MIRE therapy equipment.

SUMMARY

An infrared wound healing unit, constructed in accordance with the present invention, includes a first flexible frame member defining a first opening and a layer of an optically and radiographically transparent flexible heating element mounted to the first flexible frame member. This infrared wound healing unit also includes a power unit, comprising a housing and a battery disposed within said housing, for supplying power to the layer of an optically and radiographically transparent flexible heating element to heat the layer of an optically and radiographically transparent flexible heating element. An infrared wound healing unit, constructed in accordance with the present invention, further includes a second flexible frame member defining a second opening through which heat emitted from the layer of an optically and radiographically transparent flexible heating element passes. The first flexible frame member and the second flexible frame member are connected together for relative pivotal movement between the two about a common axis and in line-of-sight alignment. An infrared wound healing unit, constructed in accordance with the present invention, further includes means for selectively supplying power from the power unit to the layer of an optically and radiographically transparent flexible heating element and means for securing the infrared wound healing unit to a patient in proximity to the wound being treated. With this infrared wound healing unit, (a) heat emitted from the layer of an optically and radiographically transparent flexible heating element passes through the second opening of the second flexible frame member to a wound of a patient to treat the wound, (b) the wound of the patient that is being treated can be viewed while heat is emitted from the layer of an optically and radiographically transparent flexible heating element and passes through the second opening of the second flexible frame member to treat the wound, (c) the wound is accessible for other forms of treatment, and (d) the infrared wound healing unit remains secured to the patient while the wound is being viewed or treated.

DETAILED DESCRIPTION OF THE EMBODIMENTS

FIGS. 1 through 4 are various views of a first embodiment of an infrared wound healing unit constructed in accordance with the present invention. It will become apparent that this infrared wound healing unit is in the form of a disposable bandage that conforms to the shape of the body part of a patient to which it is applied.

This infrared wound healing unit includes a first flexible frame member 10 defining a first opening 10a. First flexible frame member 10 can be formed of suitable plastic material, so that when the infrared wound healing unit is applied to a body part of a patient, it conforms to the shape of the body part of the patient to which it is applied.

The infrared wound healing unit illustrated in FIGS. 1 through 4 also includes a layer 12 of an optically and radiographically transparent flexible heating element mounted to first flexible frame member 10. Layer 12 of an optically and radiographically transparent flexible heating element can be one of a number of different materials, such as tin oxide, indium tin oxide, or antimony tin oxide, and is a sputtered or evaporated deposition on a thin layer flexible membrane of polyester or like colorless optically transparent polymer which, when electrically energized, emits a uniform thermal dispersion. For the present invention, the effective deposition of the optically and radiographically transparent material can have, for example, a thickness of 1800 to 2000 Angstroms.

The planar extent and thickness of layer 12 of an optically and radiographically transparent flexible heating element are selected to provide a sufficiently strong, but flexible, layer, so that when the infrared wound healing unit is applied to a body part of a patient, it conforms to the shape of the body part of the patient to which it is applied.

Figure 1:
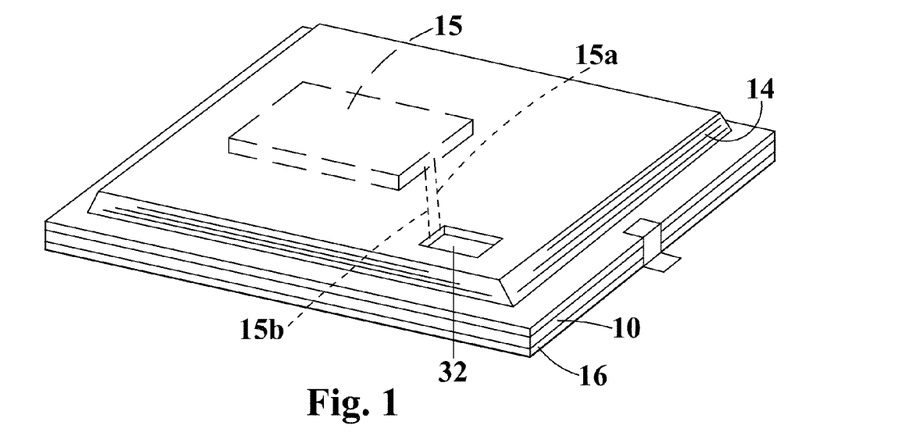
FIG. 1 is a perspective view of a first embodiment of an infrared wound healing unit, constructed in accordance with the present invention, in a fully closed condition for MIRE treatment of a wound.

Layer 12 of an optically and radiographically transparent flexible heating element can be configured in different ways that depend upon the particular application of the infrared wound healing unit. For example, layer 12 of an optically and radiographically transparent flexible heating element can be configured to cover entirely first opening 10a in first flexible frame 10, as illustrated, or partially cover the first opening in the first flexible frame member.

The infrared wound healing unit illustrated in FIGS. 1 through 4 also includes a power unit comprising a housing 14 and a battery 15 (represented by dashed lines in FIG. 1) having leads 15a and 15b (represented by dashed lines in FIG. 1) disposed within housing 14. This power unit supplies power, via leads 15a and 15b, to layer 12 of an optically and radiographically transparent flexible heating element to heat this layer and to emit infrared heat from this layer.

The infrared wound healing unit illustrated in FIGS. 1 through 4 further includes a second flexible frame member 16 defining a second opening 16a through which heat emitted from layer 12 of an optically and radiographically transparent flexible heating element passes. Second flexible frame member 16 can be formed of suitable medical grade plastic material, for example a foam polymer such as PORON sold by Roger Co., Inc., so that when the infrared wound healing unit is applied to a body part of a patient, it conforms to the shape of the body part of the patient to which it is applied. Second flexible frame member 16 serves as a spacer that prevents layer 12 of an optically and radiographically transparent flexible heating element from making contact with a wound, represented in FIGS. 3 and 4 by reference numeral 18, that is being treated.

Figure 2:
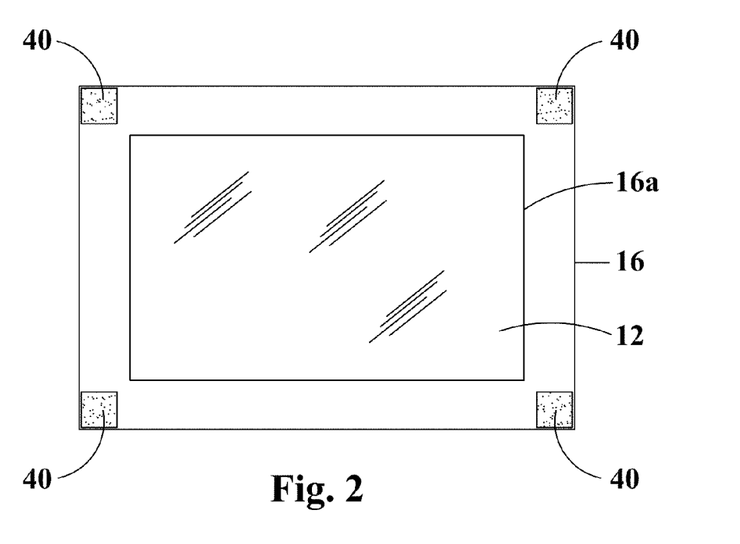
FIG. 2 is a bottom view of the FIG. 1 infrared wound healing unit.
Figure 3:
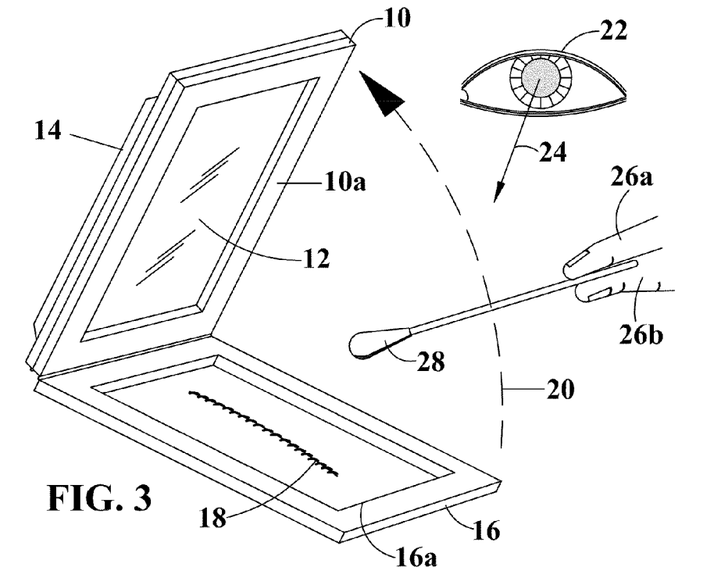
FIG. 3 is a perspective view of the FIG. 1 infrared wound healing unit in a first partially open condition for viewing and treatment of a wound by a clinician.
Figure 4:
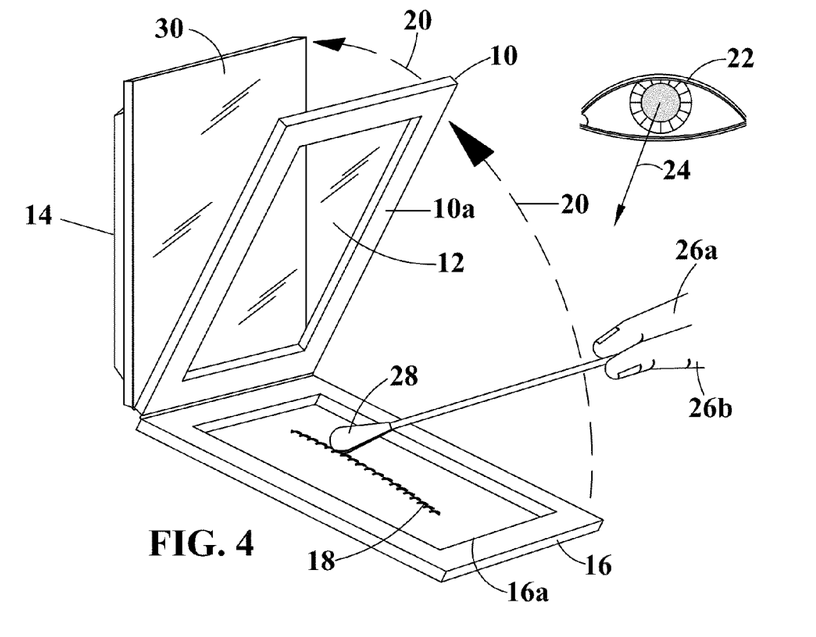
FIG. 4 is a perspective view of the FIG. 1 infrared wound healing unit in a second partially open condition for viewing and treatment of a wound by a clinician.

The infrared wound healing unit illustrated in FIGS. 1 through 4 also includes means for connecting first flexible frame member 10 to second flexible frame member 16, so that the two frame members can undergo relative pivotal movement, represented by dashed line arrows 20 in FIGS. 3 and 4, about a common axis and first opening 10a in flexible frame member 10 and second opening 16a in flexible frame member 16 are in line-of-sight alignment. As a result, heat emitted from layer 12 of an optically and radiographically transparent flexible heating element passes through second opening 16a of second flexible frame member 16 to wound 18 of a patient that is being treated and the wound of the patient that is being treated can be viewed while heat is emitted from the layer of an optically and radiographically transparent flexible heating element and passes through second opening 16a of second flexible frame member 16. This feature of the present invention is represented by an eyeball 22 and an arrow 24 in FIGS. 3 and 4. In addition, wound 18 can be treated in ways other than by the heat emitted from layer 12 of an optically and radiographically transparent flexible heating element. This feature of the present invention is represented by fingers 26a and 26b and a sanitary medical cotton swab 28 in FIGS. 3 and 4.

In the embodiment of the present invention illustrated in FIGS. 1 through 4, battery housing 14 is connected to first flexible frame member 10 and second flexible frame member 16 for relative pivotal movement between the first flexible frame member, the second flexible frame member, and the power unit about a common axis in a manner similar to the different ways the pages of a book are bound together. Various means, such as mechanical hinges or adhesive bindings, can be used to connect together first flexible frame member 10, second flexible frame member 16, and the power unit for relative pivotal movement between these three components about a common axis.

The infrared wound healing unit illustrated in FIGS. 1 through 4 preferably includes a reflective coating 30 disposed on a surface of battery housing 14 that faces layer 12 of an optically and radiographically transparent flexible heating element when the battery housing is flush against first flexible frame member 10. Reflective coating 30 reflects infrared heat emitted by layer 12 of an optically and radiographically transparent flexible heating element, that might otherwise be wasted, toward wound 18 that is being treated. Reflective coating 30 can be, for example, a metalized surface conformal textile or deposited on a transparent medical grade flexible foam such as PORON. Preferably, reflective coating 30 is covered by a coating having a high dielectric constant for a number of reasons. One is to prevent electrical shorting of layer 12 of an optically and radiographically transparent flexible heating element. A second is to eliminate the possibility of a chemical change of reflective coating 30. A third is to eliminate the occurrence of chemical reactions, caused during pharmaceutical treatment of the wound that would reduce the reflectivity of reflective coating 30, such as might occur when medications are applied to the would or chemicals are used for anti-biotic purposes.

Figure 8:
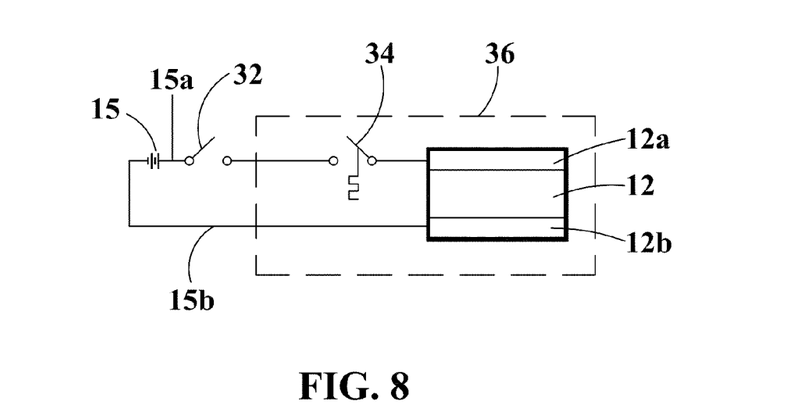
FIG. 8 is a schematic diagram of a circuit that can be used to selectively supply power to the optically and radiographically transparent flexible heating element component and regulate the temperature of the heat applied to a wound by an infrared wound healing unit constructed in accordance with the present invention.

FIG. 8 is a schematic diagram of a circuit that can be used to selectively supply power to layer 12 of an optically and radiographically transparent flexible heating element and to regulate the temperature of the infrared heat emitted by the layer 12 of an optically and radiographically transparent flexible heating element. The circuit illustrated in FIG. 8 includes a switch 32 that selectively connects battery 15, by means of leads 15a and 15b, to layer 12 of an optically and radiographically transparent flexible heating element to selectively supply power from the battery to layer 12 of an optically and radiographically transparent flexible heating element. Switch 32 can be of different well-known forms. It can be an ON/OFF switch that is accessible, as shown in FIG. 1, at the top of battery housing 14 for repeated closing and opening, or it can be a one-time release switch which, once closed, remains closed.

Also included in the FIG. 8 circuit is a thermal sensor, represented by a switch 34, that is positioned in proximity to layer 12 of an optically and radiographically transparent flexible heating element. The proximity of thermal sensor 34 to layer 12 of an optically and radiographically transparent flexible heating element is represented by dashed lines 36.

Thermal sensor 34 can be in the form of a conventional thermostat that senses the temperature in the vicinity of layer 12 of an optically and radiographically transparent flexible heating element. and closes and opens in response to temperature changes in the vicinity of layer 12 of an optically and radiographically transparent flexible heating element. Power is supplied to layer 12 of an optically and radiographically transparent flexible heating element when thermal sensor 34 is closed and the supply of power is interrupted when the thermal sensor is opened, thereby selectively connecting battery 15 to layer 12 of an optically and radiographically transparent flexible heating element and regulating the temperature of the infrared heat emitted by layer 12. Power is conducted from battery 15 to a pair of conductive strips 12a and 12b that are deposited on layer 12 of an optically and radiographically transparent flexible heating element which, in turn, conduct power to layer 12 of an optically and radiographically transparent flexible heating element. Thermal sensor 34 can be arranged to function at a single preset temperature or at a temperature, within a preset temperature range, that is selected by a clinician.

The infrared wound healing unit of FIGS. 1 through 4 further includes means for securing the infrared wound healing unit to a patient in proximity to the wound being treated. Such means can include, for example, a plurality of adhesive sectors 40 at the corners of the free surface of second flexible frame member 16 as illustrated in FIG. 2. Any of the many commercially available medical grade adhesives that are specifically arranged for contact with the skin of a patient can be used.

The infrared wound healing unit just described provides the following benefits:
 (a) a wound being treated by layer 12 of an optically and radiographically transparent flexible heating element can be viewed by a clinician without disrupting the infrared heat treatment of the wound, and
 (b) a wound being treated by layer 12 of an optically and radiographically transparent flexible heating element is accessible for other forms of treatment without removing the infrared wound healing unit from the patient being treated.

Figure 5:
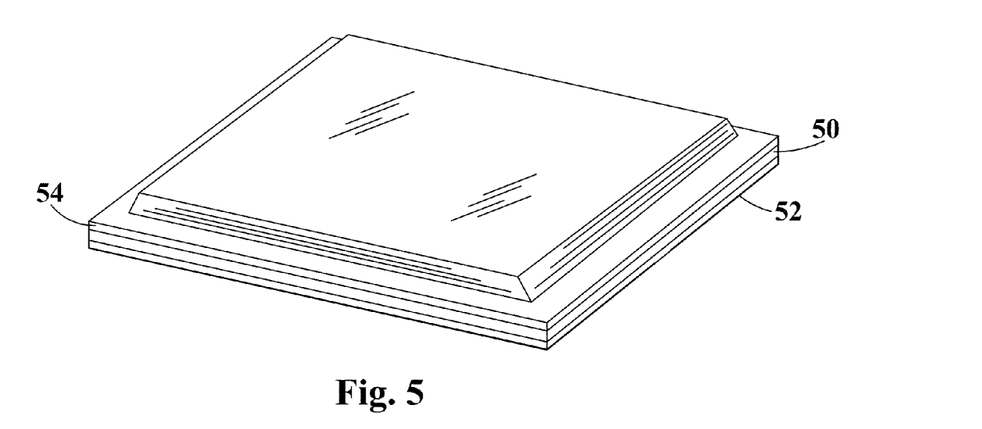
FIG. 5 is a perspective view of a second embodiment of an infrared wound healing unit, constructed in accordance with the present invention, in a fully closed condition for MIRE treatment of a wound.
Figure 6:
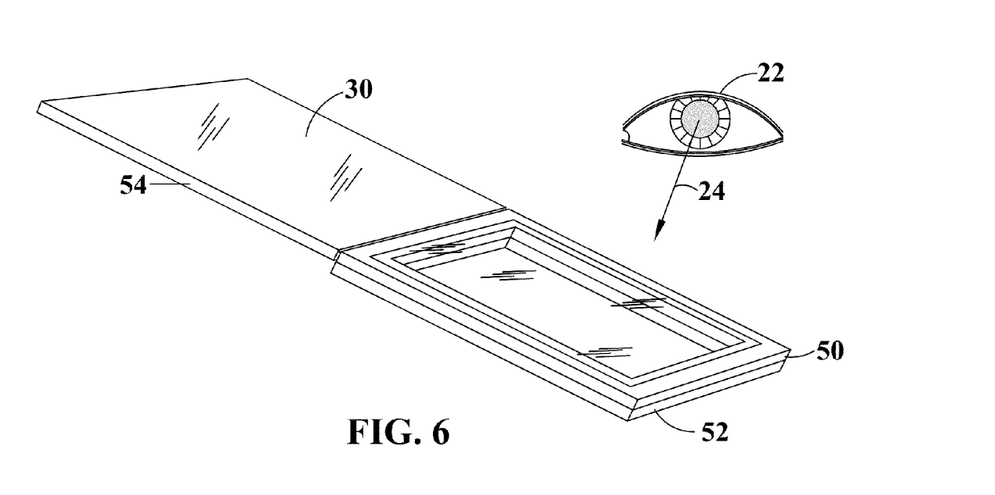
FIG. 6 is a perspective view of the FIG. 5 infrared wound healing unit in a first partially open condition for viewing of a wound by a clinician.
Figure 7:
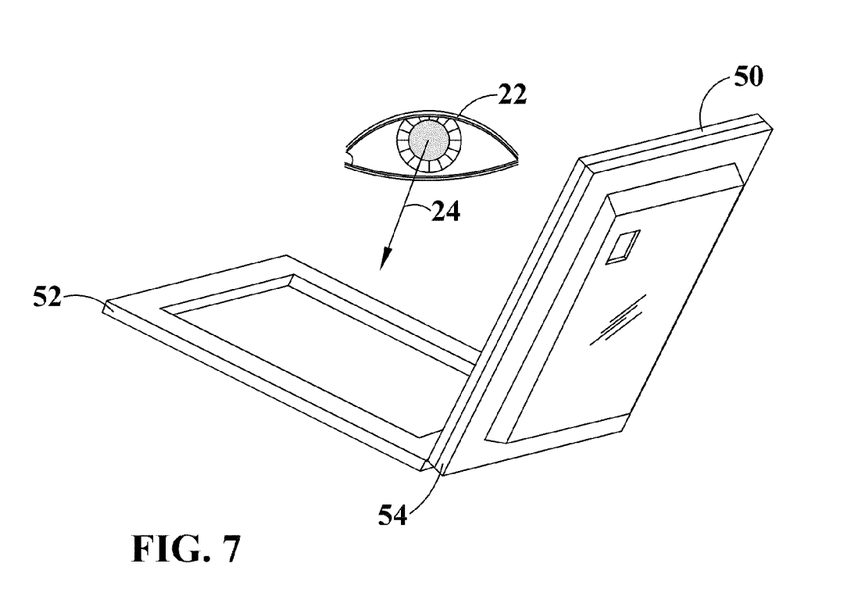
FIG. 7 is a perspective view of the FIG. 5 infrared wound healing unit in a second partially open condition for viewing and treatment of a wound by a clinician.

FIGS. 5 through 7 illustrate a second embodiment of an infrared wound healing unit constructed in accordance with the present invention. This second embodiment differs from the first embodiment in the way in which the first flexible frame member 50, the second flexible frame member 52, and the battery housing 54 are connected to one another. Instead of being held together in a manner similar to the way pages of a book are bound to one another, in the embodiment of the present invention illustrated in FIGS. 5 through 7, first flexible frame member 50 and second flexible frame member 52 are connected for relative pivotal movement about a first common axis and battery housing 54 and first flexible frame member 50 are connected for relative pivotal movement about a second common axis spaced from the first common axis. In all other respects, the two embodiments of the present invention are similar, so a more detailed description of the second embodiment is not provided.

The benefits provided by the first embodiment of the present invention that are identified above also are provided by the second embodiment of the present.

The foregoing illustrates some of the possibilities for practicing the invention. Many other embodiments are possible within the scope and spirit of the invention. It is, therefore, intended that the foregoing description be regarded as illustrative rather than limiting, and that the scope of the invention is given by the appended claims together with their full range of equivalents.

What is claimed is:

1. An infrared wound healing unit comprising:
 a first flexible frame member defining a first opening;
 a layer of an optically and radiographically transparent flexible heating element mounted to said first flexible frame member;
 a power unit, comprising a housing and a battery disposed within said housing, for supplying power to said layer of an optically and radiographically transparent flexible heating element to heat said layer of an optically and radiographically transparent flexible heating element;
 a second flexible frame member defining a second opening through which heat emitted from said layer of an optically and radiographically transparent flexible heating element passes;
 means for connecting said first flexible frame member to said second flexible frame member:
  (a) for relative pivotal movement between said first flexible frame member and said second flexible frame member about a common axis, and
  (b) in line-of-sight alignment;
 means for selectively supplying power from said power unit to said layer of an optically and radiographically transparent flexible heating element; and
 means for securing the infrared wound healing unit to a patient in proximity to the wound being treated;
 whereby:
  (a) heat emitted from said layer of an optically and radiographically transparent flexible heating element passes through said second opening of said second flexible frame member to a wound of a patient to treat the wound,
  (b) the wound of the patient that is being treated can be viewed while heat is emitted from said layer of an optically and radiographically transparent flexible heating element and passes through said second opening of said second flexible frame member to treat the wound,
  (c) the wound is accessible for other forms of treatment, and
  (d) the infrared wound healing unit remains secured to the patient while the wound is being viewed or treated.

2. An infrared wound healing unit according to claim 1 wherein said housing of said power unit is connected to said first flexible frame member and said second flexible frame member for relative pivotal movement between said first flexible frame member, said second flexible frame member, and said power unit about said common axis.

3. An infrared wound healing unit according to claim 1 wherein said housing of said power unit is connected to said first flexible frame member for relative pivotal movement between said first flexible frame member and said power unit about a second common axis spaced from said common axis.

4. An infrared wound healing unit according to claim 1 wherein said layer of an optically and radiographically transparent flexible heating element:
 (a) is selected from the group consisting of tin oxide, indium tin oxide, and antimony tin oxide, and
 (b) covers entirely said first opening in said first flexible frame member.

5. An infrared wound healing unit according to claim 2 wherein said layer of an optically and radiographically transparent flexible heating element:
 (a) is selected from the group consisting of tin oxide, indium tin oxide, and antimony tin oxide, and
 (b) covers entirely said first opening in said first flexible frame member.

6. An infrared wound healing unit according to claim 3 wherein said layer of an optically and radiographically transparent flexible heating element:
 (a) is selected from the group consisting of tin oxide, indium tin oxide, and antimony tin oxide, and
 (b) covers entirely said first opening in said first flexible frame member.

7. An infrared wound healing unit according to claim 1 further including a reflective coating disposed on a surface of said housing of said power unit that faces said layer of an optically and radiographically transparent flexible heating element when said housing of said power unit is flush against said first flexible frame member.

8. An infrared wound healing unit according to claim 2 further including a reflective coating disposed on a surface of said housing of said power unit that faces said layer of an optically and radiographically transparent flexible heating element when said housing of said power unit is flush against said first flexible frame member.

9. An infrared wound healing unit according to claim 3 further including a reflective coating disposed on a surface of said housing of said power unit that faces said layer of an optically and radiographically transparent flexible heating element when said housing of said power unit is flush against said first flexible frame member.

10. An infrared wound healing unit according to claim 1 wherein said means for selectively supplying power from said power unit to said layer of an optically and radiographically transparent flexible heating element include:
  (a) means for selectively connecting said battery to said layer of an optically and radiographically transparent flexible heating element to selectively supply power from said battery to said layer of an optically and radiographically transparent flexible heating element, and
  (b) means for regulating the amount of power supplied from said battery to said layer of an optically and radiographically transparent flexible heating element.

11. An infrared wound healing unit according to claim 2 wherein said means for selectively supplying power from said power unit to said layer of an optically and radiographically transparent flexible heating element include:
  (a) means for selectively connecting said battery to said layer of an optically and radiographically transparent flexible heating element to selectively supply power from said battery to said layer of an optically and radiographically transparent flexible heating element, and
  (b) means for regulating the amount of power supplied from said battery to said layer of an optically and radiographically transparent flexible heating element.

12. An infrared wound healing unit according to claim 3 wherein said means for selectively supplying power from said power unit to said layer of an optically and radiographically transparent flexible heating element include:
  (a) means for selectively connecting said battery to said layer of an optically and radiographically transparent flexible heating element to selectively supply power from said battery to said layer of an optically and radiographically transparent flexible heating element, and
  (b) means for regulating the amount of power supplied from said battery to said layer of an optically and radiographically transparent flexible heating element.

13. An infrared wound healing unit according to claim 10 wherein said means for regulating the amount of power supplied from said battery to said layer of an optically and radiographically transparent flexible heating element include a thermal sensor positioned in proximity to said layer of an optically and radiographically transparent flexible heating element for:
  (a) sensing the temperature in the vicinity of said layer of an optically and radiographically transparent flexible heating element, and
  (b) closing and opening in response to temperature changes in the vicinity of said layer of an optically and radiographically transparent flexible heating element to supply power to said layer of an optically and radiographically transparent flexible heating element when said thermal sensor is closed and interrupt the supply of power when said thermal sensor is opened.

14. An infrared wound healing unit according to claim 11 wherein said means for regulating the amount of power supplied from said battery to said layer of an optically and radiographically transparent flexible heating element include a thermal sensor positioned in proximity to said layer of an optically and radiographically transparent flexible heating element for:
  (a) sensing the temperature in the vicinity of said layer of an optically and radiographically transparent flexible heating element, and
  (b) closing and opening in response to temperature changes in the vicinity of said layer of an optically and radiographically transparent flexible heating element to supply power to said layer of an optically and radiographically transparent flexible heating element when said thermal sensor is closed and interrupt the supply of power when said thermal sensor is opened.

15. An infrared wound healing unit according to claim 12 wherein said means for regulating the amount of power supplied from said battery to said layer of an optically and radiographically transparent flexible heating element include a thermal sensor positioned in proximity to said layer of an optically and radiographically transparent flexible heating element for:
  (a) sensing the temperature in the vicinity of said layer of an optically and radiographically transparent flexible heating element, and
  (b) closing and opening in response to temperature changes in the vicinity of said layer of an optically and radiographically transparent flexible heating element to supply power to said layer of an optically and radiographically transparent flexible heating element when said thermal sensor is closed and interrupt the supply of power when said thermal sensor is opened.

16. An infrared wound healing unit according to claim 1 wherein said layer of an optically and radiographically transparent flexible heating element includes a plurality of conductive strips to which power from said power unit is conducted.

17. An infrared wound healing unit according to claim 2 wherein said layer of an optically and radiographically transparent flexible heating element includes a plurality of conductive strips to which power from said power unit is conducted.

18. An infrared wound healing unit according to claim 3 wherein said layer of an optically and radiographically transparent flexible heating element includes a plurality of conductive strips to which power from said power unit is conducted.

19. An infrared wound healing unit according to claim 7 further including a coating having a high dielectric constant disposed on said reflective coating.

20. An infrared wound healing unit according to claim 8 further including a coating having a high dielectric constant disposed on said reflective coating.

21. An infrared wound healing unit according to claim 9 further including a coating having a high dielectric constant disposed on said reflective coating.

* * * * *

UNITED STATES PATENT AND TRADEMARK OFFICE
CERTIFICATE OF CORRECTION

PATENT NO. : 8,328,858 B2
APPLICATION NO. : 12/767206
DATED : December 11, 2012
INVENTOR(S) : Barry E. Barsky and Jay M. Silverman It is certified that error appears in the above-identified patent and that said Letters Patent is hereby corrected as shown below:

In the Claims:

In column 6, line 46, after the word "said" the word --first-- should be inserted.

Signed and Sealed this
Fourteenth Day of May, 2013

Teresa Stanek Rea
*Acting Director of the United States Patent and Trademark Office*